United States Patent [19]
Pfeiffer et al.

[11] Patent Number: 4,565,302
[45] Date of Patent: Jan. 21, 1986

[54] ACTUATABLE DOSING MECHANISM

[75] Inventors: Peter Pfeiffer, Gaienhofen; Leo Maerte, Sipplingen, both of Fed. Rep. of Germany

[73] Assignee: Ing. Erich Pfeiffer GmbH & Co. KG, Fed. Rep. of Germany

[21] Appl. No.: 570,597

[22] Filed: Jan. 13, 1984

[30] Foreign Application Priority Data

Jan. 22, 1983 [DE] Fed. Rep. of Germany ....... 3302160

[51] Int. Cl.⁴ .............................................. B67D 5/26
[52] U.S. Cl. ...................................... 222/38; 222/29; 222/32; 222/153; 222/321; 235/94 R; 235/117 A; 239/73; 239/74
[58] Field of Search ................. 222/25, 29, 41, 36–38, 222/43, 153, 47–50, 321, 383, 385, 402.17, 402.24, 402.14, 402.13, 402.11, 402.1, 14, 16, 17, 21–23; 221/2, 4, 7, 8, 15; 239/71, 73, 74; 235/94 R, 117 B, 1 B, 61 M

[56] References Cited

U.S. PATENT DOCUMENTS

| | | | |
|---|---|---|---|
| 2,580,292 | 12/1951 | Geary et al. | 235/94 R X |
| 3,119,557 | 1/1964 | Chapman | 222/38 X |
| 3,187,963 | 6/1965 | Anderson | 222/402.24 |
| 3,419,187 | 12/1968 | Bazarnic | 222/36 |
| 3,477,561 | 11/1969 | Espinal | 206/12 |
| 3,589,563 | 6/1971 | Carragan et al. | 222/70 |
| 3,612,349 | 10/1971 | Thomas | 221/4 |
| 3,688,945 | 9/1972 | Harman, Jr. et al. | 221/8 |
| 3,797,748 | 3/1974 | Nozawa et al. | 239/321 |
| 3,831,808 | 8/1974 | Bender | 221/197 |
| 4,162,746 | 7/1979 | Anderson et al. | 222/153 |
| 4,220,247 | 9/1980 | Kramer | 222/153 X |

Primary Examiner—Joseph J. Rolla
Assistant Examiner—Kevin P. Shaver
Attorney, Agent, or Firm—Steele, Gould & Fried

[57] ABSTRACT

A dosing mechanism in the form of a manually operable, single-acting piston pump, which dispenses a given quantity of a substance, e.g. in atomized form, during each actuating stroke has a counter. For this purpose, a counting ring mounted in rotary manner on a base part is provided, which is advanced by one step per actuating stroke by an indexing device with cooperating and correspondingly bevelled ribs, so that in each case a different character in the counting ring appears at a window in the actuating pusher casing. Two projections cooperating with one another in a given position of the counting ring form a locking device against further actuation of the atomizing pump, when a given number of strokes have been performed.

18 Claims, 10 Drawing Figures

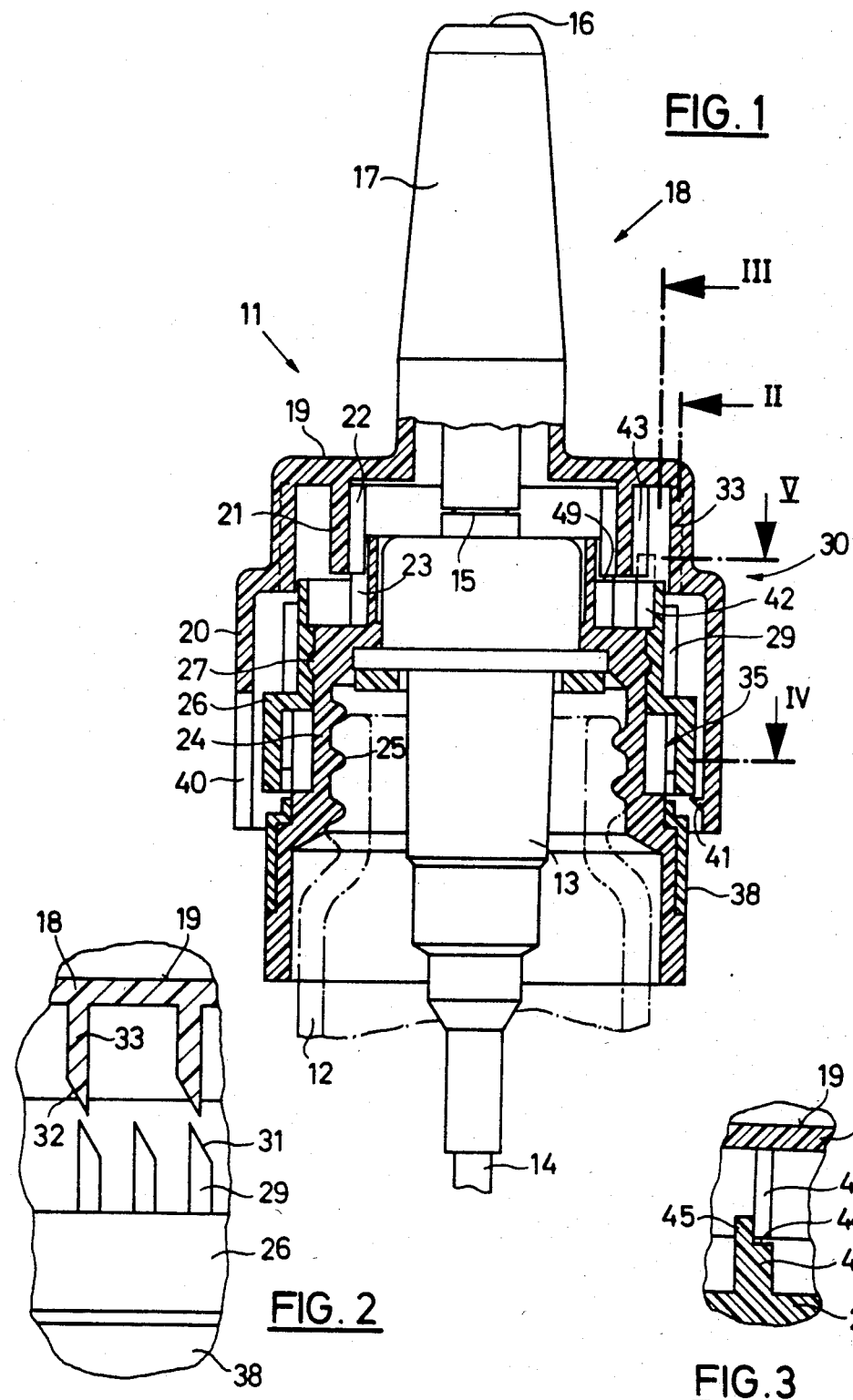

ACTUATABLE DOSING MECHANISM

BACKGROUND OF THE INVENTION

The present invention relates to an actuatable dosing or metering mechanism with an actuating pusher or trigger for dispensing a measured quantity or unit of a flowable substance from a container, particularly a dosing or atomizing pump, during each actuating stroke.

Such dosing mechanisms are used for the most varied purposes and dispensing materials, including for medical purposes. They can be dosing or atomizing pumps, which deliver and dispense, as well as optionally atomize, one unit or quantity of the material during each pump stroke. However, the dosing mechanism can also be in the form of dosing valves, which are fitted to the container with an internal pressure and open an actuation for dispensing a given quantity and then closed again.

The quantity or units dispensed during an actuating stroke can be kept constant within relatively narrow limits in the case of a suitable construction of the dosing mechanism, so that it is also possible to dose those pharmaceutical substances whose action is dependent on the dose. However, it has not hitherto been possible to prevent, through error, underdosing or overdosing by too few or too many actuating strokes, or administration of doses for excessively long periods, or in the incorrect order.

SUMMARY OF THE INVENTION

The object of the invention is to provide an actuatable dosing mechanism, which permits monitoring of precise doses and/or which largely eliminates incorrect dosing with respect to the number of doses and/or the duration dosing.

According to the invention, this object is achieved by a counter for automatically counting the actuating strokes.

Thus, the counter is started up by the actuation of the actuating pusher and can be constructed in numerous different ways. For example, it can contain an optical display, which displays the number of actuating strokes. According to an advantageous embodiment of the invention, the counter can contain a rotary counting ring, preferably with a scale. Moreover, an additional ring can be provided, which can be coupled into the counting ring, preferably by axial displacement. Thus, in addition to a number, this additional ring makes it possible to provide a second scale, e.g. in addition to a date sequence a weekday sequence. Thus, for example it is possible that with a once daily administration over a certain number of days, the counting ring can count this number of days, while the additional ring indicates the particular weekday, so that the user can always establish whether or not a dose has been administered on the particular day.

Particular preference is given to a construction with a locking device for the actuating stroke, which can be actuated as a function of the counter. For example, at the planned end of the administration period following a certain number of actuating strokes (or perhaps days), the dosing mechanism can be locked, to prevent a time-based overdosage. In this way, it is also possible to use very dose-dependent pharmaceuticals in the form of sprays, in which a precise sequence of use-days is associated with a corresponding number of use intervals.

In this way, it is also possible to carry out variable dosing operations in a simple manner, by giving beforehand these different doses through a corresponding scale and/or locking means, which can optionally also be releasable. Thus, the dosing mechanism can be provided for a dose rate decreasing during the treatment period. The provision of a releasable locking means permits administration without it being necessary for the user to count, in that the locking means is activated after a daily maximum dose of a certain number of strokes and can then be released again.

A particularly simple and advantageous embodiment of a dosing mechanism, which can be constructionally combined with a small standard manually operated atomizing pump, is preferably constructed in such a way that the dosing mechanism has a base part, the actuating pusher which is preferably axially movable with respect thereto and a counting ring surrounding the base part. An indexing device is disposed between the actuating pusher and the counting ring moving in stepwise manner during axial displacement of the actuating pusher.

Advantageously, the actuating pusher is connected in non-rotary, but axially displaceable manner with the base part. The indexing device can have bevelled indexing faces and a safety catch preferably acting on one side. The advance of the counting ring is brought about there by the bevelled indexing faces, while the catch prevents turning back. Advantageously, the catch is simultaneously oriented as a resilient arresting means for preventing an unintentional further rotation. It would also be possible to use an indexing device with positive locking against further rotation.

The safety catch can have an engaging device, which rotates the counting ring back to a given position on exceeding a predetermined rotation position. The indexing device need not perform the complete travel and instead the further rotation into the particular end position is brought about by the engaging device and is fixed there up to the next actuation.

The locking device for the actuating travel can be constructed by cooperating projections and/or faces on the actuating pusher and counting ring. Thus, if the counting ring has reached its predetermined end position, the locking device comes into action and prevents the actuating stroke. In the case of a releaseable locking device, the counting ring can have a handle, by which it can be rotated into a new starting position.

BRIEF DESCRIPTION OF THE DRAWINGS

For the purpose of illustrating the invention, there are shown in the drawings forms which are presently preferred; it being understood, however, that this invention is not limited to the precise arrangements and instrumentalities shown.

FIG. 1 is a vertical partial section through an atomizing pump.

FIG. 2 is a partial section along line II in FIG. 1.

FIG. 3 is a partial section along line III in FIG. 1.

DETAILED DESCRIPTION OF THE INVENTION

Figure 8:
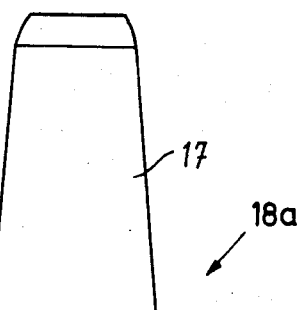
FIG. 8 is a detailed section along line VIII.

The embodiment according to FIGS. 1 to 6 shows a dosing mechanism 11 in the form of an atomizing pump, which is screwed onto a container 12 partially shown in phantom. The atomizing pump has a pump chamber 13, which is not shown in detail and into which liquid can be sucked from the interior of the container by means of a suction tube 14. Under the action of a piston passing into pump chamber 13 and which is connected to a piston rod 15, liquid is drawn into suction tube 14. The liquid is dispensed by means of an atomizing nozzle 16, which is arranged at the upper end of a slightly conical shaft 17. The shaft belongs to a plastic component which forms an actuating pusher or trigger 18 for actuating the pump. It has a wide shoulder 19, which surrounds shaft 17 and forms an actuating surface for the user's finger. From there, a stepped casing 20 passes downwards and largely surrounds the inner parts of the atomizing pump. A ring 21 projects downwards from shoulder 19 and carries on its inside vertically oriented teeth 22 having axes parallel to the pump axis, which engage with corresponding teeth 23 on a pump base 24. Ring 21 forms an axial guide for the actuating pusher, i.e. permitting axial movements, but preventing rotary movements.

Figure 6:
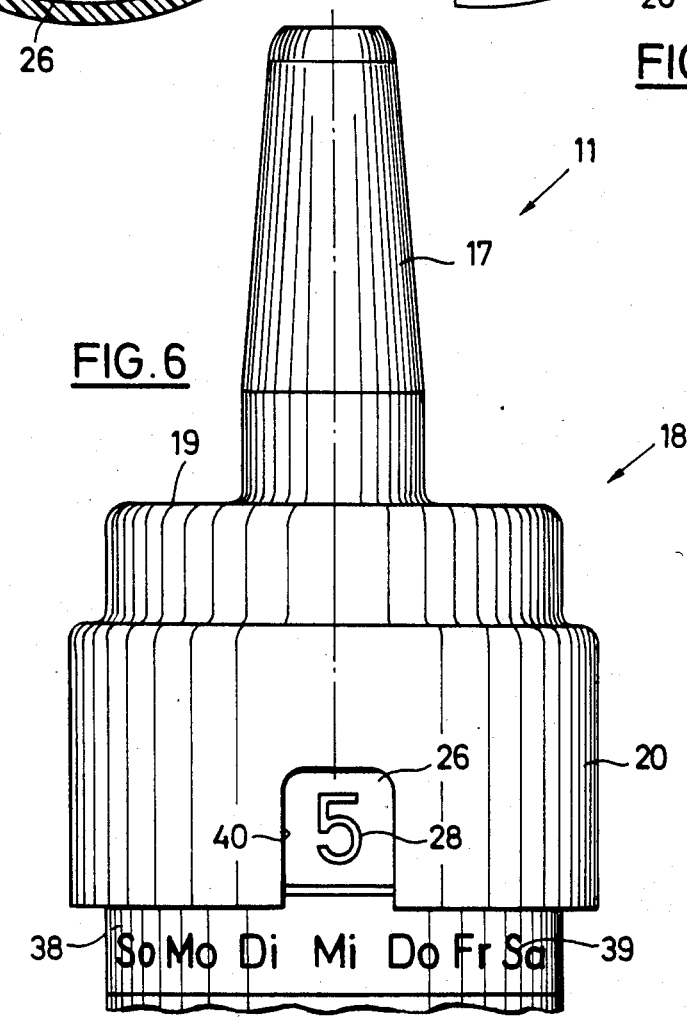
FIG. 6 is a side view of the atomizing pump according to FIG. 1.

Like all the other parts of the atomizing pump, the base is a plastic injection molding and has a thrice-stepped, upwardly tapering sleeve shape. The internal thread 25 for screwing the pump onto container 12 is located in the central region. The outside of the central step of cover 24 is surrounded by a counting ring 26, which is axially fixed on cover 24 by an annular projection 27 snapping into an annular groove on ring 26. However, it can still rotate. In a lower, somewhat outwardly projecting area of the outside of its casing, counting ring 26 carries characters 28, e.g. consisting of a continuous numbering system corresponding to the number of actuating strokes to be performed by the atomizing pump (FIG. 6). On the outside of the upper part of the counting ring are provided substantially axially directed (having axes parallel to the pump axis) ribs 29, which belong to an indexing device 30 and are arranged around the entire circumference. On their free top surface, ribs 29 have bevelled indexing faces 31 (FIG. 2), with which are associated correspondingly bevelled indexing faces 32 on inner ribs 33 in the actuating pusher. FIG. 2 shows that the number of ribs 29 is twice as large as the number of ribs 33.

A safety catch 35 (FIG. 4) is also incorporated in the indexing device 30 and comprises a notched star-shaped portion 36 in the form of external teeth on base 24, which cooperate with four resilient plastic strips 37 of counting ring 26. The plastic strips cooperate with the notched star in the manner of pawls. As a result of the shape of the teeth, which comprise relatively shallow sloping tooth profiles with an asymmetrical notch in the tooth gullet, it is assured that the sloping plastic strips automatically rotate the counting ring 26 into the position shown in FIG. 4 as a result of their natural resilience and even from a position turned by a few degrees compared with the position shown. The counting ring can rotate in a clockwise direction, but is prevented from counterclockwise rotation by the plastic strips.

Figure 2A:
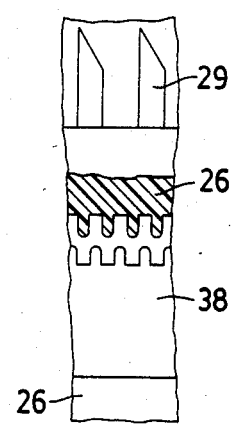
FIG. 2a is a partial section illustrating a coupling arrangement between the counting ring and the additional ring.
Figure 4:
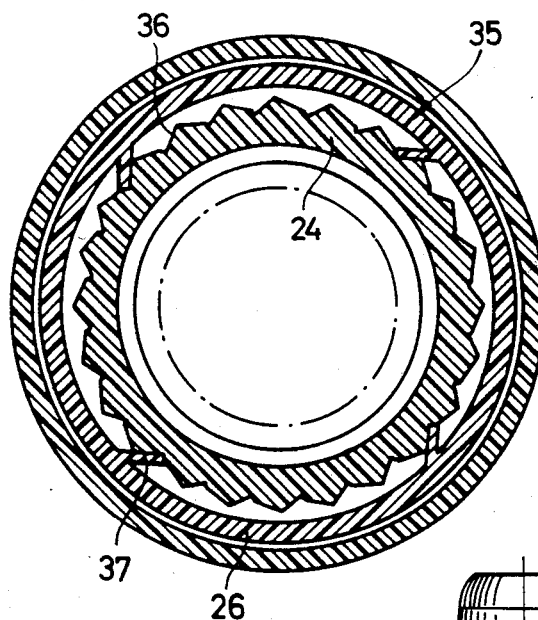
FIG. 4 is a horizontal section along line IV (without the inner part of the pump).

An additional ring 38 is also rotatably mounted on the base part and can be axially upwardly displaced. It can then be coupled by corresponding teeth into the counting ring 26, so that it rotates together with the latter. Additional ring 38 is already slidably mounted on the lower neck part of cover 24 for the purpose of being rotatable around the central axis relative to cover 24. The rotatable mounting allows axial movement of the additional ring 38 by axial sliding relative to cover 24. In FIG. 1 the position of additional ring 38 is shown uncoupled from counting ring 26. After slidably moving additional ring 38 upwardly, as described immediately hereinbefore, the additional ring 38 can be coupled by corresponding teeth, located in additional ring 38 and counting ring 26, as shown in FIG. 2a. Ring 38 can also have characters 39, e.g. in the form of weekdays (FIG. 6). The valid character 28 on counting ring 26 can be indicated by a random marking on the actuating pusher, but preferably by a window-like cutout 40 in casing 20.

A resilient spring latch 41 prevents actuating pusher 18 from being drawn upwards from the counting ring 26.

On its upper inside, counting ring 26 has an inwardly directed projection 42, which is located in the peripheral path of a corresponding projection 43 of actuating pusher 18. Axially, the projections are so dimensioned relative to one another that, when they are not cooperating, they do not prevent the axial movement of actuating pusher 18 relative to counting ring 26 or base 24. However, they do prevent the axial movement in the position of FIG. 3, in which a shoulder 44 of projection 42 cooperates with projection 43. A stop member 45 of projection 42 extending upwards beyond shoulder 44 prevents a further rotation of the counting ring over and beyond the locking position shown in FIG. 3. Thus, stop members 43, 42 form a locking means for the actuating stroke of the atomizing pump.

Figure 5:
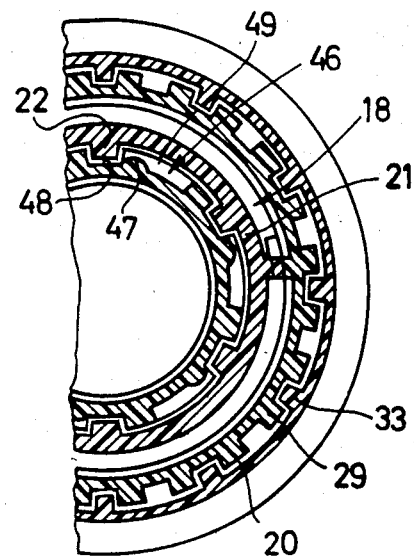
FIG. 5 is a horizontal partial section along line V in FIG. 1 (also without the inside part of the pump).

FIG. 5 also shown that a transfer securing means 46 is provided which, on rotating actuating pusher 18 with respect to the base part relative to the operating position shown in FIG. 5, acts in the clockwise direction and prevents actuation. There is then a movement of the teeth 22 on the actuating pusher, while overcoming a bulge-like projection 47, into a position in which they no longer pass into the groove 48 corresponding thereto and are instead prevented from any axial movement by a locking face 49. The bulge-like projections prevent accidental rotation out of the corresponding transport and actuation position.

The function of the embodiment according to FIGS. 1 to 6 is as follows. Dosing mechanism 11 is normally fixed to container 12, which is filled with a corresponding quantity of a substance to be dispersed. This can be a liquid, but can also be other flowable substances up to paste or cream form, which are then not atomized and are instead merely dispensed at a discharge opening. It is preferred that the pump chamber is already filled, so that dispensing takes place during the first actuating stroke. However, it would also be possible to intentionally provide initial suction strokes, before the actual count commences.

For transportation purposes, the atomizing pump is secured by a certain clockwise pivoting of actuating pusher 18 compared with the position of FIG. 5, so that its teeth or ribs 22 project over the locking face 49. For putting into operation, the actuating pusher is made operational by rotating counterclockwise and into the position shown in FIG. 5. If the container is e.g. filled with a pharmaceutical substance, which is taken in by means of the mucous membranes of the nose, shaft 17 is introduced into the nasal cavity and the pump is actuated by pressure on shoulder 19. Ribs 22 pass into grooves 48 and do not prevent the axial movement during the actuating stroke, but secure the actuating pusher against rotation. There is a simultaneous engagement between the sloping faces 31, 32 of ribs 29, 33 and transfer counting rings 26 of FIG. 2 to the left by a distance which is somewhat smaller than that between the ribs 29. The plastic strips 37 are at the same time transported over the apex of the tooth of the notched star 36 adjacent thereto. During the return stroke, after atomizing the substance to be dispensed by the atomizing nozzle 16, the two ribs 29, 33 are again disengaged and the plastic strips 37 pass downwards on the sloping tooth profile and rotate the notched star further into a position corresponding to FIG. 4. In this position, the next-following number 28 and the next-following character 39 on additional ring 38 are in the vicinity of window 40.

The additional ring has been upwardly displaced compared with the position shown in FIG. 1, namely into a position in which the characters 28 and 29 match one another (e.g. date and weekday).

This cycle is repeated until projections 42 and 43 are in the position according to FIG. 3. This takes place after a number of actuating strokes corresponding to the use cycle. In the case of a 3 week period of use, this position would be reached e.g. after the 21st stroke and the pump would then be locked against further use. As in the represented embodiment no handle is shown for resetting the pump again, the use period would be at an end. Stop member 45 prevents any accidental further rotation. In the case of a pharmaceutical substance, whose use is to be repeated after a given time, stop member 45 could be replaced by a powerful catch, which could be overridden by manual rotation of the counting ring 26 provided with a handle, so that the use cycle could recommence.

Figure 7:
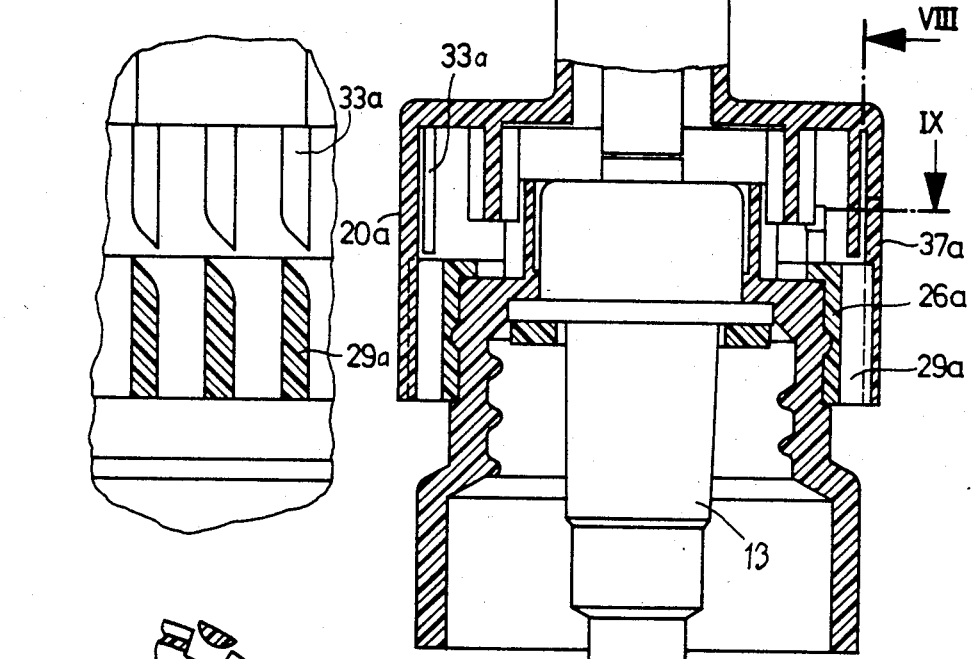
FIG. 7 is a vertical partial section through another embodiment.
Figure 9:
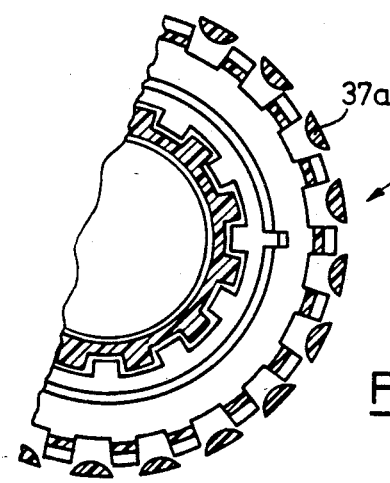
FIG. 9 is a horizontal detailed section along line IX (without the inside part of the pump).

FIGS. 7 to 9 show another embodiment. In these drawings, the same parts carry the same reference numerals, while in the case of similar parts, the letter "a" is added. In order to avoid unnecessary repetition, reference should be made to the preceding description.

In this embodiment, casing 20a of actuating pusher 18a and counting ring 26a are axially shorter. Ribs 29a on counting ring 26a are thicker in the radial direction and apart from cooperating with the indexing ribs 33 on their outer periphery, constructed as individual, freestanding, axially directed webs. Ribs 33 cooperate with stop springs 37a, which are shaped like leaf spring-shaped strips and are formed by axially directed cuts in casing 20a. The number of these plastic spring strips 37a corresponds to the number of ribs 29a, so that a safety catch 35a is formed.

This construction is particularly simple. However, in the present embodiment, there is no securing means against backward rotation. However, this could be brought about by an asymmetrical configuration of the plastic spring strips 37a. Like the catch 35 in the embodiment according to FIGS. 1 to 6, catch 35a also fulfills the function of indexing into a given rotation position during each stroke. In order to achieve a good spring action, a recess is provided within these strips which separates them from ribs 33. While the design of this embodiment is otherwise the same, it has no additional ring.

What is claimed is:

1. An actuatable dosing mechanism with an actuating pusher for dispensing a quantity of a flowable substance from a container during each actuating stroke of the actuating pusher, the dosing mechanism comprising:
   a counter for automatically counting the actuating strokes; and,
   a locking device between the counter and the actuating pusher for disabling the actuating pusher to prevent further dispensing of the substance after a predetermined number of actuating strokes.

2. A dosing mechanism according to claim 1, wherein the locking device comprises cooperating projections on the actuating pusher and the counter.

3. A dosing mechanism according to claim 1, wherein the counter is rotatable in only one direction, the counter having resilient strips which engage a notched surface to prevent rotation of the counter opposite to the only one direction.

4. A dosing mechanism according to claim 1, comprising securing means for preventing the axial movement of the actuating pusher during transportation, the securing means being engageable by rotation of the actuating pusher relative to all remaining parts of the dosing mechanism.

5. A dosing mechanism according to claim 1, wherein the mechanism is an atomizing pump, and further comprising a pump base cap for mounting the mechanism, the pump base cap bearing the counter.

6. A dosing mechanism according to claim 1, wherein the locking device comprises cooperating faces on the actuating pusher and the counter.

7. A dosing mechanism according to claim 1, further comprising means for releasing the locking device.

8. An actuatable dosing mechanism with an actuating pusher for dispensing a quantity of a flowable substance from a container during each actuating stroke of the actuating pusher, comprising: a rotary counting ring for automatically counting the actuating strokes; and, an additional ring which can be coupled to the counting ring by axial displacement of the additional ring.

9. A dosing mechanism according to claim 8, wherein the counting ring bears characters and the actuating pusher comprises a casing projecting over the counting ring, the casing being rotatably mounted on the base and having a window exposing one of the characters.

10. A dosing mechanism according to claim 8, further comprising securing means on the counting ring for preventing the axial movement of the actuating pusher during transportation, the securing means being engageable by rotation of the actuating pusher relative to all remaining parts of the dosing mechanism.

11. A dosing mechanism according to claim 8, wherein the counting ring is rotatable in only one direction, the counting ring having resilient strips which engage a notched surface to prevent rotation of the counting ring opposite to the only one direction.

12. A dosing mechanism according to claim 8, wherein the mechanism is an atomizing pump, and further comprising a pump base cap for mounting the mechanism, the pump base cap bearing the counting ring.

13. A dosing mechanism according to claim 8, wherein the locking device comprises cooperating faces on the actuating pusher and the counting ring.

14. A dosing mechanism according to claim 8, further comprising means for releasing the locking device.

15. An actuatable dosing mechanism with an actuating pusher for dispensing a quantity of a flowable substance from a container during each actuating stroke of the actuating pusher comprising: a base part, the actuating member being axially movable relative to the base part;

a counting ring surrounding the base part; and, an indexing device operationally disposed between the actuating pusher and the counting ring, the indexing device rotating in steps during the axial displacement of the actuating pusher, the counting ring and the indexing device forming a counter for automatically counting the actuating strokes.

16. A dosing mechanism according to claim 15, wherein the base part and the actuating pusher are connected to one another by means permitting the relative axial displacement but preventing relative rotation.

17. A dosing mechanism according to claim 15, wherein the indexing device comprises bevelled indexing faces and a safety catch acting in only direction, the safety catch having an engaging device for turning the counting ring into a given position on exceeding a predetermined rotation position.

18. A dosing mechanism according to claim 17, wherein the safety catch comprises a notch star-shaped portion and resilient plastic strips.

* * * * *

UNITED STATES PATENT AND TRADEMARK OFFICE
CERTIFICATE OF CORRECTION

PATENT NO. : 4,565,302

DATED : January 21, 1986

INVENTOR(S) : Peter Pfeiffer and Leo Maerte

It is certified that error appears in the above-identified patent and that said Letters Patent is hereby corrected as shown below:

Column 1, line 17 before "actuation" delete "an" and insert --on--.

Column 4, line 56 delete "dispersed" and insert --dispensed--.

Column 8, line 9 after "only" insert --one--.

Signed and Sealed this

Second Day of September 1986

[SEAL]

Attest:

DONALD J. QUIGG

Attesting Officer

Commissioner of Patents and Trademarks